(12) United States Patent
Galin

(10) Patent No.: US 6,730,691 B1
(45) Date of Patent: May 4, 2004

(54) USES OF ALPHA ADRENERGIC BLOCKING AGENTS

(76) Inventor: Miles A. Galin, 345 E. 37th St., 3rd Floor, New York, NY (US) 10016

(*) Notice: Subject to any disclaimer, the term of this patent is extended or adjusted under 35 U.S.C. 154(b) by 0 days.

(21) Appl. No.: 09/501,400

(22) Filed: Feb. 10, 2000

(51) Int. Cl.⁷ .............................................. A61K 31/415
(52) U.S. Cl. ...................................... 514/392; 514/912
(58) Field of Search .................................. 514/392, 912

(56) References Cited

U.S. PATENT DOCUMENTS

| | | | |
|---|---|---|---|
| 3,658,963 A | 4/1972 | Turner et al. | 424/311 |
| 3,966,779 A | 6/1976 | Satzinger et al. | 260/404 |
| 4,252,721 A | 2/1981 | Silvestrini et al. | 260/243.3 |
| 4,310,524 A | 1/1982 | Wiech et al. | 424/244 |
| 4,336,396 A | 6/1982 | Giordano et al. | 560/20 |
| 4,443,441 A | 4/1984 | Galin | 424/244 |
| 4,490,379 A | 12/1984 | Podos et al. | 424/262 |
| 4,795,758 A | 1/1989 | Danree et al. | 514/428 |
| 4,818,772 A | 4/1989 | Pontagnier et al. | 514/651 |
| 4,879,294 A | 11/1989 | Schoenwald | 514/253 |
| 4,879,304 A | 11/1989 | Schoenwald | 514/374 |
| 5,041,446 A | 8/1991 | Silvestrini | 514/255 |
| 5,116,615 A | 5/1992 | Gokeen et al. | 424/94.2 |
| 5,182,270 A | 1/1993 | Musson et al. | 514/58 |
| 5,234,927 A | 8/1993 | Galli Angeli et al. | 514/253 |
| 5,288,759 A | 2/1994 | DeSantis, Jr. | 514/603 |
| 5,302,172 A | 4/1994 | Sage, Jr. et al. | 604/20 |
| 5,321,012 A | 6/1994 | Mayer et al. | 514/25 |
| 5,336,678 A | 8/1994 | Cavallini | 514/275 |
| 5,433,958 A | 7/1995 | Grislain et al. | 424/436 |
| 5,446,070 A | 8/1995 | Mantelle | 514/772.6 |
| 5,451,609 A | 9/1995 | Bellamy et al. | 514/651 |
| 5,459,133 A | 10/1995 | Neufeld | 514/215 |
| 5,460,828 A | 10/1995 | Santus et al. | 424/489 |
| 5,488,050 A | 1/1996 | Neufeld | 514/236.2 |
| 5,512,577 A | 4/1996 | Roche et al. | 514/281 |
| 5,514,672 A | 5/1996 | Bazzano | 514/168 |
| 5,545,626 A | 8/1996 | Stein et al. | 514/44 |
| 5,556,838 A | 9/1996 | Mayer et al. | 514/25 |
| 5,561,154 A | 10/1996 | Bellamy et al. | 514/546 |
| 5,565,466 A | 10/1996 | Gioco et al. | 514/280 |
| 5,571,177 A | 11/1996 | Deacon et al. | 623/6 |
| 5,612,027 A | 3/1997 | Galin et al. | 424/78.04 |
| 5,620,416 A | 4/1997 | Riviere | 604/49 |
| 5,624,961 A | 4/1997 | Ban et al. | 514/651 |
| 5,635,172 A | 6/1997 | Jani et al. | |
| 5,654,281 A | 8/1997 | Mayer et al. | 514/25 |
| 5,656,286 A | 8/1997 | Miranada et al. | 424/449 |
| 5,660,851 A | 8/1997 | Domb | 424/427 |
| 5,719,197 A | 2/1998 | Kanios et al. | 514/772.6 |
| 5,731,339 A | 3/1998 | Lowrey | 514/400 |
| 5,759,532 A | 6/1998 | Galin et al. | 424/78.04 |
| 5,766,580 A | 6/1998 | Galin et al. | 424/78.04 |
| 5,776,445 A * | 7/1998 | Cohen et al. | 424/78.04 |
| 5,795,909 A | 8/1998 | Shashoua et al. | 514/449 |
| 5,811,547 A | 9/1998 | Nakamichi et al. | 540/589 |
| 5,853,751 A | 12/1998 | Masiz | 424/449 |
| 5,899,875 A | 5/1999 | Millot et al. | 604/20 |
| 5,965,152 A | 10/1999 | Galin et al. | 424/426 |
| 5,972,326 A | 10/1999 | Galin et al. | 424/78.04 |
| 6,273,092 B1 | 8/2001 | Nolan | |
| 6,540,990 B2 | 4/2003 | Nolan | |

FOREIGN PATENT DOCUMENTS

WO    8910126    11/1989

OTHER PUBLICATIONS

"Drugs in the management of disease of the eye" [retrieved on Sep. 26, 2003] Retrieved from the Internt:< URL: http://www.hucmlrc.howard edu/Pharmacology/handouts/DRUGS%20IN%20THE%20MANAGEMENT%20OF%20DISEASES%20OF%20THE%20EYE.htm>.

Fraunfelder FW et al., 2003, "Possible adverse effects of drugs used in refractive surgery" *J Cataract Refract Surg* 29(1):170–175.

Westfall DP, "Adrenergic Agonists and Antagonists" [retrieved on Sep. 26, 2003] Retrieved from the Internt <URL: http://www.unr.edu/med/dept/pharmacology/medpharm/SectionII_Autonomic/IIDAdrenoceptors20–24.pdf>.

Fan–Paul NI et al., 2002, "Night vision disturbances after corneal refractive surgery" *Surv Ophthalmol* 47(6):533–546.

Rockman HA et al., 2002, "Seven–transmembrane–spanning receptors and heart function" *Nature* 415(6868):206–212.

Chou BS et al., "The role of pupil meeting in refractive surgery" [retrieved on Sep. 26, 2003] Retrieved from the Internt: <URL: http://www.lasikinfocenter.net/Pupil%20Size/The%20Role%20of%20Pupil%20Size%20in%20Refractive%20Surgery.htm>.

(List continued on next page.)

*Primary Examiner*—Zohreh Fay
(74) *Attorney, Agent, or Firm*—Baker Botts LLP

(57) ABSTRACT

Disclosed are methods and compositions for inhibiting undesirable visual anomalies commonly experienced by individuals who have undergone refractive eye surgery, including photophobia, glare, secondary images and haloing. In particular, the disclosure provides for topically applying an ophthalmic solution to the eye wherein the ophthalmic solution contains a therapeutically effective amount of one or more alpha adrenergic blocking agents, preferably thymoxamine. The disclosure further provides for an ophthalmic solution containing one or more alpha adrenergic blocking agents in a physiologically acceptable carrier, which can be administered to a subject at an effective dose to be therapeutically effective in concentration and rate of release. An ophthalmic solution for inhibiting one or more visual anomalies experienced by an individual who has undergone refractive eye surgery containing a therapeutically effective amount of one or more alpha adrenergic blocking agents in combination with one or more anti-irritant agents and/or one or more anti-inflammatory agents is also disclosed.

14 Claims, No Drawings

OTHER PUBLICATIONS

Chou BS, 2001, "Turn around these LASIK letdowns: here are some of the problems that may occur and how you can manage them" [retrieved on Sep. 27, 2003] Retrieved from the Internt: <URL: http://www.revoptom.com/body/articles/10_2001/ro257.htm>.

Ellerton CR et al., 2001, "Postoperative complications of excimer laser photorefractive keratectomy for myopia" *Ophthalmol Clin North Am* 14(2):359–76, ix.

McDonald JE 2nd et al., 2001, "Effect of brimonidine tartrate ophthalmic solution 0.2% on pupil size in normal eye under different luminance conditions" *J Cataract Refract Surg* 27(4):560–564.

Melki SA et al., 2001, "LASIK complications: etiology, management, and prevention" *Surv Ophthalmol* 46(2):95–116.

Nagy ZZ et al., 2001, "Photorefractive keratectomy for hyperopia in 800 eyes with the meditec MEL 60 laser" *J. Refract. Surg.* 17:525–533.

Nagy ZZ et al., 2001, "Treatment of intraocular pressure elevation after photorefractive keratectomy" *J Cataract Refract Surg* 27(7):1018–1024.

Chou B et al., 2000, "Influence of accommodation on pupil size: method of controlling night glare and halos?" ASCRS scientific paper. Boston: Society of Cataract and Refractive Surgery 2000, Abstract No. 889; [retrieved on Sep. 29, 2003] Retrieved from the Internt: <URL: http://www.ascrs.org/abstracts/show_paper.asp?id=834>.

Geerling G et al., 2000, "Relative mydriasis after photorefractive keratectomy" *J. Refract. Surg.* 16:69–74.

Boxer Wachler BS et al., 1999, "Improvement of visual function with glare testing after photorefractive keratectomy and radial keratotomy" *Am J Ophthalmol* 128(5):582–587.

Ghaith AA et al., 1998, "Contrast sensitivity and glare disability after radial keratotomy and photorefractive keratectomy" *Arch Ophthalmol* 116(1):12–18.

Martinez CE et al., 1998, "Effect of pupillary dilation on corneal optical aberrations after photorefractive keratectomy" *Arch Ophthalmol* 116(8):1053–1062.

*Encyclopedia of Molecular Biology and Molecular Medicine*, vol. 1, p. 289–290 (Robert A. Meyers ed., VCH Publishers 1996/7).

*Molecular Cell Biology* pp. 870–874 (Harvey Lodish et al. eds. 3rd ed., W.H. Freeman and Company 1995).

*McGraw–Hill Dictionary of Scientific and Technical Terms*, pp. 38, 47 (Sybil P. Parker ed., 5th ed., McGraw–Hill, Inc. 1994).

Cotecchia S et al., 1990, "Multiple second messenger pathways of α–adrenergic receptor subtupes expressed in eukaryotic cells" *J. Biol. Chem.* 265(1):63–69.

*Biochemistry*, pp. 1146–1147, 1154–1155 (Donald Voet et al. eds., John Wiley & Sons 1990).

Weiner N, "Drugs that Inhibit Adrenergic Nerves and Block Adrenergic Receptors" in *The Pharmacological Basis of Therapeutics* pp. 145–180 (Gilman, Goodman, Rall, and Murad, eds. MacMillan Publishing Co. 1985).

Weiner N, "Drugs that Inhibit Adrenergic Nerves and Block Adrenergic Receptors" in *The Pharmacological Basis of Therapeutics* pp. 181–214 (Gilman, Goodman, Rall, and Murad, eds. MacMillan Publishing Co. 1985); and.

Alster et al. "Dapiprazole for Pateints with Night Haloes after Excimer Keratectomy", *Graefe's Arch Clin Exp Ophthalmol* vol. 234, 1996, pp S. 139–S. 141.

Wand et al., "Thymoxamine Test Differentiating Angle–Closure Glaucoma From Open–Angle Glaucoma With Narrow Angles", *Arch Ophthalmol*, vol. 96, Jun. 1978, pp. 1009–1011.

Wand et al., "Thymoxamine Hydrochloride: An Alpha–adrenergic Blocker", Kramer, Ed., *Survey of Ophthalmology*, vol. 25, No. 2, Sep.–Oct. 1980, pp. 75–84.

Saheb et al., "Effect of thymoxamine and pilocarpine on the depth of the anterior chamber", *Can J Ophthalmol*, vol. 15, Oct. 1980, pp. 170–171.

Drugs Under Surveillance—Generic Names (http://www.open.gov.uk/mca/dsurgen.htm) printed Jul. 6, 1999, 3 pages.

Ocular Pharmacology (http://www.eye.ttu.edu/Lectures/Crosson_OcPharm.html) printed Jul. 6, 1999, 7 pages.

Saggerson et al., "Effect of compound D–600 (methoxyverapamil) on gluconeogenesis and on acceleration of the process by alpha–adrenergic stimuli in rat kidney tubules", *Biochem. J.*, vol. 190 (1980) pp. 283–291, Abstract, 1 page.

Eyeson–Annan et al., "Comparative pupil dilaton using phenylephrine alone or in combination with tropicamide", *Ophthalmology*: vol. 105, No. 4, Apr. 1998 (as appeared at http://www.supersight.com/journal/Ophthalol/9804/9544648.shtml) printed Jul. 6, 1999, 2 pages.).

Rx Ophthalmics (http://www.nutramax.com/Rx_Ophthalmics.htm), printed Jul. 6, 1999, 4 pages.

ESIR newsletter—#3—Jun. 1998—. . . tributions from the advisory board (http://esir.com/newsletter/jun98/7.htm) printed Jul. 6, 1999, 2 pages.

Drug R & D News Digest, Oct. 1997(http://sdic.sookmyung.ac.kr/NEWS/jan_feb_98/rd.htm) printed Jul. 6, 1999, 6 pages.

Representation–Erregierre (http://www.interchemical.com/erregi.html) printed Jul. 6, 1999, 1 page.

* cited by examiner

USES OF ALPHA ADRENERGIC BLOCKING AGENTS

INTRODUCTION

The present invention relates to methods and compositions for inhibiting undesirable visual anomalies commonly experienced by individuals who have undergone refractive eye surgery. Specifically, the methods and compositions of the invention provide a means for inhibiting photophobia, glare, secondary images and haloing. The methods of the invention comprise the post-operative administration of an ophthalmic solution comprising alpha adrenergic blocking agents to the surface of the eye. The invention is based on the observation that when alpha adrenergic blocking agents are applied to the surface of the eye, the composition is well tolerated and the pupil is made smaller by relaxing the iris without induced myopia. The invention further provides for the use of an ophthalmic solution comprising alpha adrenergic blocking agents to eliminate symptoms developed by conditions wherein the diameter of the pupil exceeds the diameter desired for the respective optic zone. The present invention, by enabling a method for the use of an ophthalmic solution comprising alpha adrenergic blocking agents, provides a safer and less severe treatment than those methods that utilize the administration of pilocarpine or other compositions that forcibly make the pupil smaller.

BACKGROUND OF THE INVENTION

The long-term success of refractive eye surgery is currently limited by the high incidence of undesirable visual anomalies, such as photophobia, glare, secondary images and haloing, experienced by individuals who have undergone refractive eye surgery. Refractive procedures include and are not limited to the surgical implantation of an intraocular lens, laser surgery, and radial keratotomy. Post-operative complications exist because the refractive procedure causes a differential between the corrected optic zone and the diameter of the pupil. Such a differential generally leads to persistent incidence of undesirable visual anomalies, particularly in certain situations, including but not limited to mesopic conditions of reduced illumination and, conversely, conditions of bright light experienced while driving a motor vehicle at night.

A method of treating individuals who experience undesirable visual anomalies after refractive eye surgery does not exist without causing induced myopia and headaches caused by contraction of the ciliary body associated with the application of pilocarpine or other compositions that forcibly make the pupil smaller. These agents may create risk of retinal detachment as well as photopsia. It is known that pilocarpine has been used after an ophthalmologist has induced dilation of the pupil in order to forcibly hasten the return of the iris at the conclusion of an examination or procedure to a constricted state. It is also known that dapiprazole, manufactured by Storz Instruments Co. (which was acquired by Bausch & Lomb) under the tradename Rev Eyes, is used to hasten the return of the pupil to normal size after dilation by an examiner. To Applicant's knowledge, the product Rev Eyes is instilled in the patient by the physician or optometrist in the doctor's office. Further, this product is limited by its short shelf life. Unfortunately, though the cyclotonic agents hasten the return of the iris to a normal position, they create induced myopia and cause headaches in patients. Most patients suffer from the side-effects associated with the usage of these conventional drugs.

It is known that alpha adrenergic blocking agents have been used for the treatment of angle closure glaucoma, which condition causes an increased pressure within the eyeball causing a gradual loss of sight. It is also known that alpha adrenergic blocking agents, such as thymoxamine, have been used to reverse mydriasis induced by sympathomimetic agents during the implantation of an intraocular lens in order to increase the success of fixating the lens inside the eye. Other anti-mydriatic uses of thymoxamine are discussed in Wand & Grant, Arch. Ophthalmol. 96:1009–1011 (July 1978) and Wand & Grant, Surv. Ophthalmol. 25(2):75–84 (Sept.–Oct. 1980). To Applicant's knowledge, it has not been known that alpha adrenergic blocking agents may be used to eliminate undesirable visual anomalies experienced by patients who have undergone refractive eye surgery.

There has been a long felt need since the inception of refractive procedures to eliminate undesirable visual anomalies experienced by patients who have undergone refractive eye surgery.

SUMMARY OF THE INVENTION

The present invention provides compositions and methods for using an ophthalmic solution comprising alpha adrenergic blocking agents that inhibit undesirable visual sequelae commonly experienced by individuals who have undergone refractive eye surgery. The invention further provides for the use of an ophthalmic solution comprising alpha adrenergic blocking agents to eliminate symptoms developed by conditions wherein the diameter of the pupil exceeds the diameter desired for the respective optic zone. Specifically, the compositions and methods of the invention provide a means for inhibiting photophobia, glare, secondary images and haloing.

Accordingly, the methods of the present invention comprise topically applying an ophthalmic solution to the eye wherein the ophthalmic solution contains a therapeutically effective amount of one or more alpha adrenergic blocking agents to an individual who has undergone refractive eye surgery. Moreover, the composition may be topically applied in approximately a one drop dose, which may be instilled on an as needed basis depending upon the concentration and rate of release of the one or more alpha adrenergic blocking agents within the ophthalmic solution.

In yet another embodiment of the invention, the methods comprise topically applying an ophthalmic solution to the eye wherein the ophthalmic solution contains a therapeutically effective amount of one or more alpha adrenergic blocking agents to an individual who has one or more symptoms developed by a condition wherein the diameter of the pupil exceeds the diameter desired for the respective optic zone of the eye. Such conditions include but are not limited to post surgical persistent mydriasis, traumatic mydriasis, anisocoria, photorefractive keratectomy, treatment of aphakia, and certain cases of cataract extraction and retinal detachment.

The invention further provides for compositions comprising one or more alpha adrenergic blocking agents in a physiologically acceptable carrier, which can be administered to a subject at an effective dose to be therapeutically effective in concentration and rate of release. The compositions used in the practice of the present invention comprise both rapid and sustained release of an effective dose.

In another embodiment, the alpha adrenergic blocking agents may be used preoperatively in cases where small pupils are demanded. This is particularly valuable in refractive implantation, glaucoma surgery, and keratoplasty to mention a few.

In an alternative non-limiting embodiment, the invention further provides for compositions comprising a therapeutically effective amount of one or more alpha adrenergic blocking agents in combination with one or more anti-irritant agents and/or one or more anti-inflammatory agents.

The invention is based on the observation that administration of one or more alpha adrenergic blocking agents to the surface of the eye is well tolerated and is effective in eliminating one or more undesirable visual problems without experiencing a change in focal length, headache, photopsia, floaters, etc, which are ordinarily experienced with induced cyclotonic miosis. The present invention, by enabling a method for use of an ophthalmic solution comprising one or more alpha adrenergic blocking agents, provides a safer, less risky, and asymptomatic treatment than experienced with the administration of pilocarpine or other compositions that forcibly make the pupil smaller.

DETAILED DESCRIPTION OF THE INVENTION

The present invention relates to compositions and methods for inhibiting one or more undesirable visual anomalies commonly experienced by patients who have undergone refractive eye surgery. The invention further relates to compositions and methods for inhibiting one or more symptoms developed by a condition wherein the diameter of the pupil exceeds the diameter desired for the respective optic zone of an eye. Subjects treated with an ophthalmic solution comprising one or more alpha adrenergic blocking agents have experienced reduced visual anomalies due to a relaxation of the iris causing a reduction in the diameter of the pupil without inducing myopia caused by forcibly making the pupil smaller.

The compositions and methods of the present invention provide a means for inhibiting photophobia, glare, secondary images and haloing, as well as other symptoms developed wherein the pupil diameter exceeds the desired diameter, while avoiding the adverse side effects, such as induced myopia, headaches, photopsia, retinal, detachment, and floaters, associated with the use of pilocarpine or other cyclotonic compositions that forcibly make the pupil smaller.

Compositions suitable for use in the present invention include ophthalmic solutions comprising a therapeutically effective amount of one or more alpha adrenergic blocking agents. More specifically, a therapeutically effective amount means an amount sufficient to relax the iris to reduce the diameter of the pupil thereby inhibiting one or more undesirable visual anomalies experienced by an individual who has undergone refractive eye surgery. The effective amounts of one or more alpha adrenergic blocking agents is well within the capability of those skilled in the art and may be adjusted depending upon the number, kind and concentration of the one or more alpha adrenergic blocking agents, and upon the intended duration of use from rapid to sustained delivery of the ophthalmic solution.

Suitable alpha adrenergic blocking agents among others include thymoxamine (thymoxamine hydrochloride), phentolamine (phentolamine hydrochloride), azapetine (azapetine hydrochloride), phenoxybenzamine (phenoxybenzamine hydrochloride), clonidine (clonidine hydrochloride), and tolazoline (tolazoline hydrochloride). In a preferred embodiment, the one or more alpha adrenergic blocking agents includes thymoxamine. The one or more alpha adrenergic blocking agents for use in the practice of this invention are commercially available.

A suitable ophthalmic solution containing one or more alpha adrenergic blocking agents is one having a concentration of the agent of from about 0.1% to about 1% by weight. It is preferred that the ophthalmic solution containing the one or more alpha adrenergic blocking agents has a concentration of the agent of about 0.5% by weight. The preferred solvent is water. An exemplary aqueous ophthalmic solution would have a pH of about 5.6–7 and would be clear and colorless.

The amount of composition administered is also dependent upon the subject to whom the ophthalmic solution is administered and the judgement of the physician overseeing the subject. It should be noted, however, that one of the advantages of the inventive compositions and methods allows for the subject to self administer the ophthalmic solution prior to experiencing the circumstances that ordinarily result in one or more undesirable visual anomalies.

In general the total dosage range of the one or more alpha adrenergic blocking agents should be such as to achieve a sufficient period of duration in order to inhibit the one or more undesirable visual anomalies for the duration of the desired period. Adjustments of the number and kind of the one or more alpha adrenergic blocking agents in the ophthalmic composition, the overall and relative concentrations of the one or more alpha adrenergic blocking agents in the ophthalmic composition, and the frequency of application are contemplated herein. It may be necessary to use dosages outside the ranges disclosed herein in some cases as will be apparent to those of ordinary skill in the art.

The composition may be administered by a physician or by the individual in need thereof in order to inhibit one or more undesirable visual anomalies, including photophobia, glare, secondary images and haloing, on a regular basis or on an as needed basis, and may be administered before or after experiencing the one or more visual anomalies. In a preferred embodiment of the invention, the one or more alpha adrenergic blocking agents is delivered to the eye in an ophthalmic solution by topically applying the solution in approximately a one drop dose. The approximately one drop dose may be thereafter topically applied on an as needed basis. The dosage may vary in amount and frequency depending upon the concentration and rate of release of the one or more alpha adrenergic blocking agents within the ophthalmic solution.

The compositions for use in accordance with the present invention may be formulated in a conventional manner using one or more physiologically acceptable carriers. Physiologically acceptable carriers include viscoelastic polymers, as described in U.S. Pat. Nos. 5,972,326, 5,965,152, 5,766,580, 5,759,532, and 5,612,027, the disclosures of which are incorporated herein by reference. In addition, other suitable carriers presently known in the art including solvents such as water are contemplated.

The present invention provides for novel compositions comprising a physiologically acceptable carrier for one or more alpha adrenergic blocking agents for the rapid and sustained release of the one or more alpha adrenergic blocking agents in doses sufficient to reduce or ameliorate the one or more undesirable visual anomalies in a subject in need thereof.

Further, the present invention provides for novel compositions comprising any of the above-described ophthalmic solutions further containing one or more anti-irritant agents and/or one or more anti-inflammatory agents. Suitable anti-irritant agents include naphthazoline, oxymetazoline, and tetrahydrozaline. Suitable anti-inflammatory agents include dexamethasone, fluoromethalone, loteprednol, prednisone, and diclofenac. It is preferred that the ophthalmic solution contain one or more anti-irritant agents in a concentration of from about 0.025% by weight to about 0.1% by weight. It is preferred that the ophthalmic solution contain one or more anti-inflammatory agents in a concentration of from about 0.5% by weight to about 1% by weight. It is preferred that the ophthalmic solution containing a combination of one or more anti-irritant agents with one or more anti-inflammatory agents contain a concentration of from about 0.025% by weight to about 0.1% by weight of the anti-irritant agents and from about 0.25% by weight to about 1% by weight of the anti-inflammatory agents.

The following describes experimental data relating to the administration of alpha adrenergic blocking agents to individuals following refractive eye surgery.

A suitable ophthalmic solution was prepared containing about 0.5% by weight thymoxamine by the Moorfields Eye Hospital, London, England having the following composition:

| | |
|---|---:|
| Thymoxamine Hydrochloride: | 500 mg |
| Sodium Acetate NF: | 90 mg |
| Boric Acid NF: | 1610 mg |
| Phenylmercuric Nitrate NF: | 2 mg |
| Purified Water USP q.s. to: | 100 ml |

Applicant believes that the aqueous ophthalmic solution was prepared by dissolving the sodium acetate, boric acid and phenylmercuric nitrate in most of the purified water. Dissolution was promoted by heating the solution. Upon cooling the solution to room temperature, the thymoxamine hydrochloride was added and was dissolved without further heating. The remainder of the purified water was then added to reach a final volume of 100 ml. Sterilization of the solution was achieved by filtering it through a sterilizing filter.

Three subjects, each of whom had undergone surgical implantation of a refractive intraocular lens, were selected for study. Each of the three subjects complained of experiencing photophobia, glare, secondary images and haloing, especially at night. Each of the three subjects received an approximately one drop dose twice daily of an ophthalmic solution containing 0.5% by weight of thymoxamine.

After the administration of a dosage of the ophthalmic solution, subjects experienced mild irritation from the topical application of the ophthalmic solution to the eye. Each of the subjects reported an elimination of the previously complained of undesirable visual anomaly, without experiencing induced myopia or headaches for a one day period.

Each of the subjects continued application of approximately a one drop dose on an as needed basis for a period of one month. None of the subjects have experienced the previously complained of undesirable visual anomaly during the usage period of the ophthalmic solution.

Once treatment was terminated, the one or more undesirable visual anomalies returned to each of the three subjects.

In addition, two patients who had undergone radial keratotomy and who each experienced glare and halos were similarly treated with comparable results.

The present invention is not to be limited in scope by the specific embodiments described herein which are intended as single illustrations of individual aspects of the invention, and functionally equivalent methods and components are within the scope of the invention. Indeed, various modifications of the invention, in addition to those shown and described herein will become apparent to those skilled in the art from the foregoing description. Such modifications are intended to fall within the scope of the claims. Various publications are cited herein, the contents of which are hereby incorporated, by reference, in their entireties.

I claim:

1. A method of inhibiting one or more undesirable visual anomalies experienced by an individual who has undergone refractive eye surgery comprising:

topically applying an ophthalmic solution to the eye wherein the ophthalmic solution comprises a therapeutically effective amount of thymoxamine.

2. The method of claim 1 wherein the one or more undesirable visual anomalies is selected from the group consisting of photophobia, glare, secondary images and haloing.

3. The method of claim 1 wherein the refractive eye surgery is selected from the group consisting of surgical implantation of an intraocular lens, laser surgery and radial keratotomy.

4. The method of claim 1 wherein the ophthalmic solution further comprises an alpha adrenergic blocking agent selected from the group consisting of phentolamine, azapetine, phenoxybenzamine, clonidine and tolazoline.

5. The method of claim 1 wherein the ophthalmic solution is topically applied in approximately one drop dose.

6. The method of claim 5 wherein the approximately one drop dose is topically applied on an as needed basis.

7. An ophthalmic solution for inhibiting one or more undesirable visual anomalies experienced by an individual who has undergone refractive eye surgery comprising a therapeutically effective amount of one or more alpha adrenergic blocking agents and one or more anti-irritant agents.

8. The ophthalmic solution of claim 7 wherein the one or more anti-irritant agents is selected from the group consisting of naphthazoline, oxymetazoline, and tetrahydrozaline.

9. The ophthalmic solution of claim 7 wherein the concentration of the one or more anti-irritant agents is from about 0.025% to about 0.1% by weight.

10. An ophthalmic solution for inhibiting one or more undesirable visual anomalies experienced by an individual who has undergone refractive eye surgery comprising a therapeutically effective amount of one or more alpha adrenergic blocking agents and one or more anti-inflammatory agents.

11. The ophthalmic solution of claim 10 wherein the one or more anti-inflammatory agents is selected from the group consisting of dexamethasone, fluoromethalone, loteprednol, prednisone, and diclofenac.

12. The ophthalmic solution of claim 10 wherein the concentration of the one or more anti-inflammatory agents is from about 0.5% to about 1% by weight.

13. An ophthalmic solution for inhibiting one or more undesirable visual anomalies experienced by an individual who has undergone refractive eye surgery comprising a therapeutically effective amount of one or more alpha adrenergic blocking agents, one or more anti-irritant agents, and one or more anti-inflammatory agents.

14. The ophthalmic solution of claim 13 wherein the concentration of the one or more anti-irritant agents is from about 0.025% to about 0.1% by weight and the concentration of the one or more anti-inflammatory agents is from about 0.25% to about 1% by weight.

* * * * *